(12) United States Patent
Eidenschink et al.

(10) Patent No.: US 7,487,579 B2
(45) Date of Patent: Feb. 10, 2009

(54) METHODS OF MAKING MEDICAL DEVICES

(75) Inventors: Thomas C. Eidenschink, Rogers, MN (US); Eric B. Stenzel, Tuam (IE)

(73) Assignee: Boston Scientific Scimed, Inc., Minneapolis, MN (US)

(*) Notice: Subject to any disclaimer, the term of this patent is extended or adjusted under 35 U.S.C. 154(b) by 586 days.

(21) Appl. No.: 10/386,747

(22) Filed: Mar. 12, 2003

(65) Prior Publication Data
US 2004/0181236 A1 Sep. 16, 2004

(51) Int. Cl.
*B23P 11/00* (2006.01)
*B23P 19/00* (2006.01)

(52) U.S. Cl. ............... 29/515; 29/516; 29/517; 29/821; 623/1.13; 623/1.2; 72/402

(58) Field of Classification Search ........... 29/821, 29/515, 516, 517; 148/558; 623/1.13, 1.2, 623/1.42; 72/402
See application file for complete search history.

(56) References Cited

U.S. PATENT DOCUMENTS

| | | | |
|---|---|---|---|
| 3,436,803 A * | 4/1969 | Sarnoff ............... 29/432.2 |
| 3,470,604 A * | 10/1969 | Zenick ............... 29/447 |
| 3,741,820 A | 6/1973 | Hebel, Jr. et al. |
| 4,425,908 A | 1/1984 | Simon |
| 4,968,359 A | 11/1990 | Hebel, Jr. et al. |
| 5,195,969 A | 3/1993 | Wang et al. |
| 5,234,457 A | 8/1993 | Andersen |
| 5,270,086 A | 12/1993 | Hamlin |
| 5,366,504 A | 11/1994 | Andersen et al. |
| 5,411,613 A * | 5/1995 | Rizk et al. ............... 148/606 |
| 5,456,666 A | 10/1995 | Campbell et al. |
| 5,546,646 A * | 8/1996 | Williams et al. ......... 29/407.08 |
| 5,674,242 A | 10/1997 | Phan et al. |
| 5,674,276 A | 10/1997 | Andersen et al. |
| 5,722,979 A * | 3/1998 | Kusleika ............... 623/1.11 |
| 5,725,570 A | 3/1998 | Heath |
| 5,891,507 A * | 4/1999 | Jayaraman ............... 427/2.25 |
| 6,033,380 A | 3/2000 | Butaric et al. |
| 6,063,092 A * | 5/2000 | Shin ............... 606/108 |
| 6,141,855 A * | 11/2000 | Morales ............... 29/516 |
| 6,309,402 B1 | 10/2001 | Jendersee et al. |
| 6,360,577 B2 | 3/2002 | Austin |
| 6,517,889 B1 * | 2/2003 | Jayaraman ............... 427/2.24 |
| 6,524,333 B1 * | 2/2003 | Claren et al. ............... 623/1.11 |
| 6,585,759 B1 * | 7/2003 | Baum et al. ............... 623/1.18 |
| 6,745,445 B2 * | 6/2004 | Spilka ............... 29/407.08 |
| 6,821,549 B2 * | 11/2004 | Jayaraman ............... 427/2.24 |
| 2003/0099765 A1 * | 5/2003 | Jayaraman ............... 427/2.24 |
| 2003/0150250 A1 * | 8/2003 | Shortt ............... 72/235 |
| 2003/0215564 A1 * | 11/2003 | Heller et al. ............... 427/2.25 |

FOREIGN PATENT DOCUMENTS

JP 09000522 A * 1/1997

OTHER PUBLICATIONS

"Design and Optimisation of an Ultrasonic Die System for Forming Metal Cans".

(Continued)

*Primary Examiner*—Jermie E Cozart
(74) *Attorney, Agent, or Firm*—Crompton, Seager & Tufte, LLC

(57) ABSTRACT

A method of manufacturing a medical device, such as an endoprosthesis, includes reducing the size of the medical device, and vibrating the device. In embodiments, the device is vibrated ultrasonically.

47 Claims, 7 Drawing Sheets

OTHER PUBLICATIONS

"The Ultrasonic Transducer System", undated.

"Vibratory Stress Relief-Massage for Your Workpieces".

"Formula 62 Resonant Vibration Method for Reducing Residual Stresses in Welded or Machined Fabrications", Vibration Shaping the Future, Schelde Exotech bv Brochure, undated.

* cited by examiner

METHODS OF MAKING MEDICAL DEVICES

TECHNICAL FIELD

The invention relates to methods of making medical devices, such as, for example, stents and stent-grafts.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprosthesis include stents and covered stents, sometimes called "stent-grafts".

Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon expandable endoprosthesis. The balloon can be inflated to deform and to fix the expanded endoprosthesis at a predetermined position in contact with the lumen wall. The balloon can then be deflated, and the catheter withdrawn.

In another technique, a self-expandable endoprosthesis is formed of an elastic material that can be reversibly compacted and expanded, e.g., elastically or through material phase transition. During introduction into the body, the endoprosthesis is restrained in a compacted condition on a catheter or a delivery shaft. Upon reaching the desired implantation site, the restraint is removed, for example, by retracting a restraining device such as an outer sheath, enabling the endoprosthesis to self-expand by its own internal elastic restoring force.

During delivery, an endoprosthesis is typically attached to a catheter, preventing the endoprosthesis from slipping off or shifting on the catheter, which can cause loss of the endoprosthesis, and/or lead to inaccurate and imprecise delivery of the prosthesis. Attachment of the endoprosthesis can include mechanically clamping or crimping the endoprosthesis on the catheter.

SUMMARY

The invention relates to methods of making medical devices. The invention features a method of attaching an endoprosthesis, such as a stent or a stent-graft, to a catheter.

In one aspect, the invention features a method of manufacturing an endoprosthesis including reducing the size of the endoprosthesis, and vibrating the endoprosthesis.

Embodiments include one or more of the following features. The endoprosthesis is vibrated ultrasonically. The endoprosthesis is reduced in size and vibrated simultaneously or sequentially. The reduction in size of the endoprosthesis attaches the endoprosthesis to a catheter. The reduction in size of the endoprosthesis secures the endoprosthesis to a balloon. The endoprosthesis is vibrated at harmonic or subharmonic frequencies. The endoprosthesis is vibrated at multiple frequencies. The endoprosthesis is vibrated at one or more frequencies that vary as a function of time.

The entire endoprosthesis can be reduced in size, or only a portion of the endoprosthesis is reduced in size.

The endoprosthesis can be vibrated from within the endoprosthesis and/or externally of the endoprosthesis.

The method can further include heating and/or cooling the endoprosthesis.

Vibratory energy can be directed to the endoprosthesis through a gaseous medium, a liquid medium, a plasma, or a supersaturated vapor medium.

The endoprosthesis can include a stent or a stent-graft, e.g., one having a drug-releasing layer.

Reducing the size of endoprosthesis can include contacting the endoprosthesis in a longitudinal direction with a member, e.g., contacting the endoprosthesis in a longitudinal direction with a roller having a groove.

In another aspect, the invention features a method of manufacturing an endoprosthesis including radially reducing the size of the endoprosthesis, and applying energy to the endoprosthesis.

Embodiments may include one or more of the following features. The energy is ultrasonic energy. Radially reducing the size of the endoprosthesis secures the endoprosthesis to a balloon. The reduction in size and the application of energy are performed simultaneously. The method further includes heating the endoprosthesis. The endoprosthesis includes a stent, e.g., one having a drug-releasing layer.

In another aspect, the invention features an apparatus for manufacturing a medical device, including a first device capable of applying a radial inward force to an endoprosthesis, and a second device capable of applying vibratory energy to the endoprosthesis.

Embodiments may include one or more of the following features. The second device is capable of applying vibratory, e.g., ultrasonic, energy. The second device includes a transducer. The second device contacts the first device. The apparatus further includes a heater capable of heating the endoprosthesis.

In another aspect, the invention features a method including providing an endoprosthesis including a metal body and a polymer layer, and applying vibratory energy to the endoprosthesis.

Embodiments may include one or more of the following features. The polymer layer is on an outside surface of the metal body. The polymer layer includes a drug or other pharmaceutical compound. The polymer layer is a continuous polymer tubular member. The polymer includes polytetrafluoroethylene. The method further includes crimping the endoprosthesis, wherein vibratory energy is applied during crimping. The method further includes crimping the endoprosthesis, and wherein vibratory energy is applied after crimping. The endoprosthesis is balloon-expandable. Vibratory energy is applied by contacting a vibrating member to the endoprosthesis. The vibratory energy has a frequency of less than about 1,000 kiloHertz, including harmonic and/or subharmonic frequencies. For example, the vibratory energy can range from about 20 Hz to about 200 kHz.

In another aspect, the inventions features a method including providing an expandable medical device, and applying vibratory energy to the medical device.

In another aspect, the invention features a method including contacting an endoprosthesis with a member having a peripheral groove, wherein the endoprosthesis is reduced in size, e.g., radial size.

Embodiments may include one or more of the following features. Contacting the endoprosthesis includes moving the member and/or the endoprosthesis along the axial or longitudinal length of the endoprosthesis. The member is a circular disc. The method further includes vibrating the endoprosthesis and/or the member, e.g., with ultrasonic energy. The method includes contacting the endoprosthesis with multiple members. The members can be arranged about a perimeter or circumference of the endoprosthesis.

In another aspect, the invention features a method including contacting an endoprosthesis with a member having an opening, wherein the endoprosthesis passes through the opening and is reduced in size, e.g., radial size.

Embodiments may include one or more of the following features. The opening is tapered. The opening has an input side having a diameter greater than a diameter of an output side. Contacting the endoprosthesis includes moving the member and/or the endoprosthesis along the axial or longitudinal length of the endoprosthesis. The method includes contacting the endoprosthesis with multiple members, e.g., arranged in series. The method further includes vibrating the endoprosthesis and/or the member, e.g., with ultrasonic energy.

The methods described herein can further include reducing the size of the medical device, e.g., a medical balloon or a filter.

Embodiments may have one or more of the following advantages. The endoprosthesis can be well secured to a catheter in a relatively low profile. Recoiling or shortening of the endoprosthesis can be reduced during expansion. Lower crimping forces may be used, which can reduce damage, e.g., to the endoprosthesis, a drug-releasing layer on the endoprosthesis, and/or a balloon to which the endoprosthesis may be attached. Vibratory energy may relieve residual stress in the endoprosthesis, thereby enhancing the structural integrity endoprosthesis, e.g., by reducing the occurrence of cracks or failure. Relieving residual stress can also make the endoprosthesis softer and more flexible, which can enhance the trackability of the endoprosthesis through a tortuous path.

Other aspects, features, and advantages of the invention will be apparent from the description of the preferred embodiments thereof and from the claims.

DETAILED DESCRIPTION

Figure 1A:
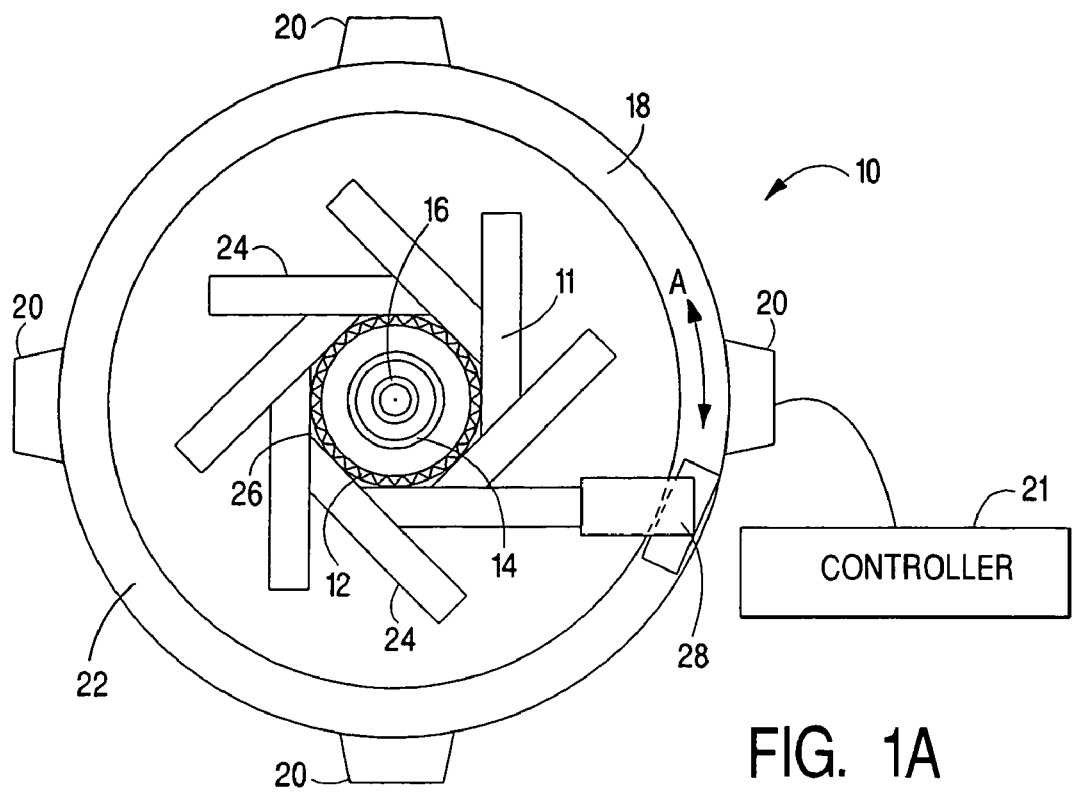
FIGS. 1A and 1B schematically illustrate a method of making a medical device.
Figure 1B:
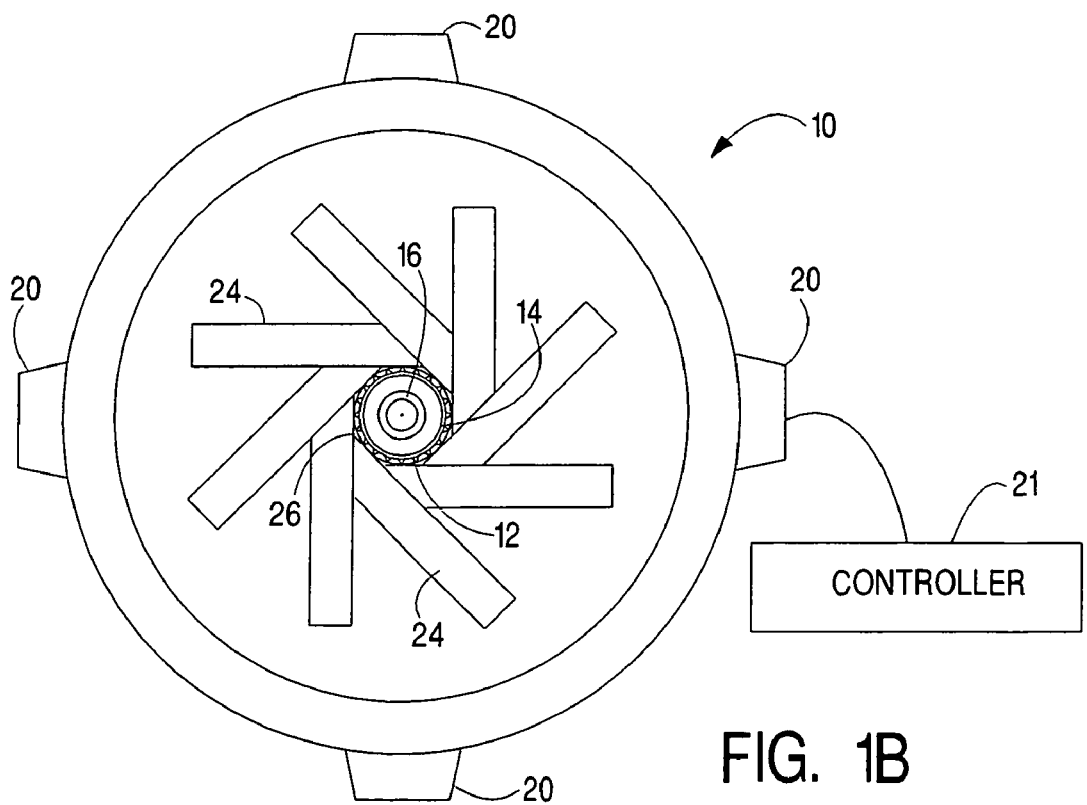

FIGS. 1A and 1B show an apparatus 10 for making a medical device, in particular, for attaching, e.g., by crimping, a stent 12 (typically made of a metal) to a catheter system 11 having a balloon 14 (typically made of polymer) carried by a catheter 16. Apparatus 10 generally includes a stent crimping device 18, a plurality of vibrators 20 (as shown, four ultrasonic vibrators) connected to the device, and a controller 21 configured to control the stent crimping device and the vibrators. Stent crimping device 18 is capable of radially compressing stent 12 to reduce its diameter, and, in this example, bring the stent into contact with balloon 14. Vibrators 20 provide energy to device 18, e.g., in the form of ultrasonic vibrations, that is then transmitted to stent 12, balloon 14, and catheter 16.

The use of vibratory energy during the crimping process can provide enhanced securement of stent 12 to balloon 14. For example, vibrations can help stent 12 to settle into balloon 14, providing a quilt-like, embedment effect. This embedment can reduce the profile of stent 12 crimped on balloon 14, which allows the stent to travel well through tortuous paths in the body. In some cases, the embedment can reduce shortening or recoiling of the stent during expansion since the stent is temporarily nested in balloon 14 and expands with the balloon.

Vibratory energy can reduce frictional binding between stent 12 and crimping device 18, and/or between stent 12 and balloon 14 during crimping. As a result, in some embodiments, the amount of force needed to crimp stent 12 may be reduced. Reducing the amount of crimping force can reduce damage to balloon 14 (e.g., by reducing the formation of pin holes) and lessen the chance of structural damage to stent 12 during manufacturing and during use. Ultrasonic energy may also reduce residual stress in stent 12, e.g., as in annealing. In embodiments in which stent 12 includes a releasable therapeutic agent or a pharmaceutically active compound, reducing the amount of crimping force can reduce damage to the stent (e.g., by lessening smearing or squeeze out) and/or provide a relatively uniform drug coating.

Stent crimping device 18 is configured to radially compress stent 12. Device 18 generally includes an actuation plate 22 and a plurality of blades 24 (as shown, eight) coupled to the actuation plate. Blades 24 are configured to engage with each other to define a polygonal aperture 26 that receives stent 12. In some embodiments, blades 24 can be configured, e.g., with curved surfaces, to define a substantially circular aperture. The size of aperture 26 may be varied to receive an uncompressed stent 12 and to crimp the stent. FIG. 1B shows apparatus 10 after stent 12 has been reduced in size. Each blade 24 is connected to actuation plate 22 by an actuation device 28 (only one shown) having links that convert rotational motion of the actuation plate (arrow A) to inward and outward motion of the blade along the radius of aperture 26. For example, clockwise rotation of actuation plate 22 may cause blades 24 to move inwardly, thereby narrowing aperture 26 and crimping stent 12; and counter-clockwise rotation of the actuation plate may cause the blades to move outwardly and widen the aperture. For a balloon-expandable endoprosthesis, crimping device 18 plastically reduces the diameter of the endoprosthesis into contact with the balloon. For a self-expandable endoprosthesis, crimping device 18 elastically reduces the diameter of the endoprosthesis so that a restraint can be positioned to maintain the small diameter configuration during delivery.

Figure 2:
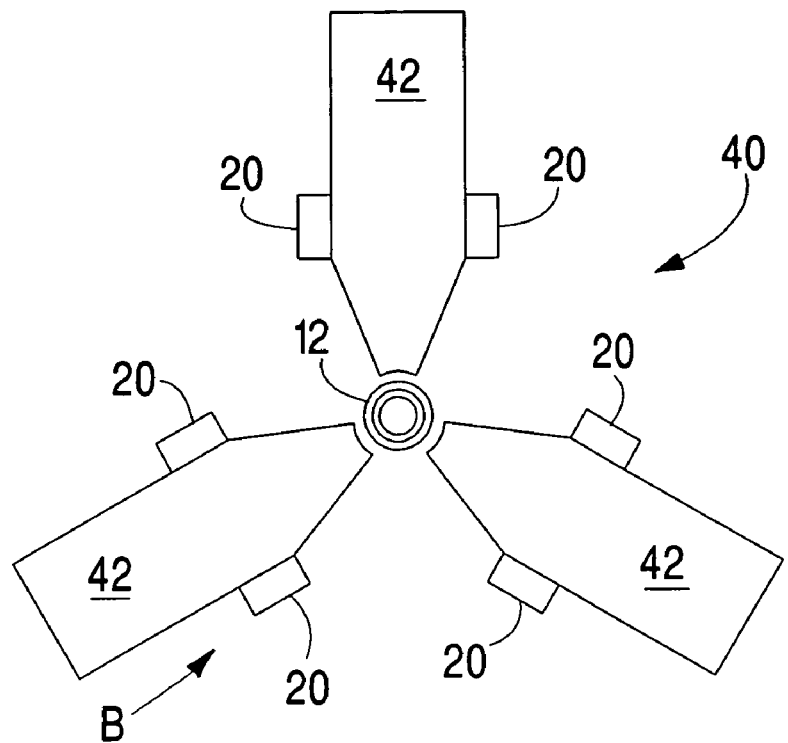
FIG. 2 schematically illustrates an embodiment of an apparatus for making a medical device.
Figure 3:
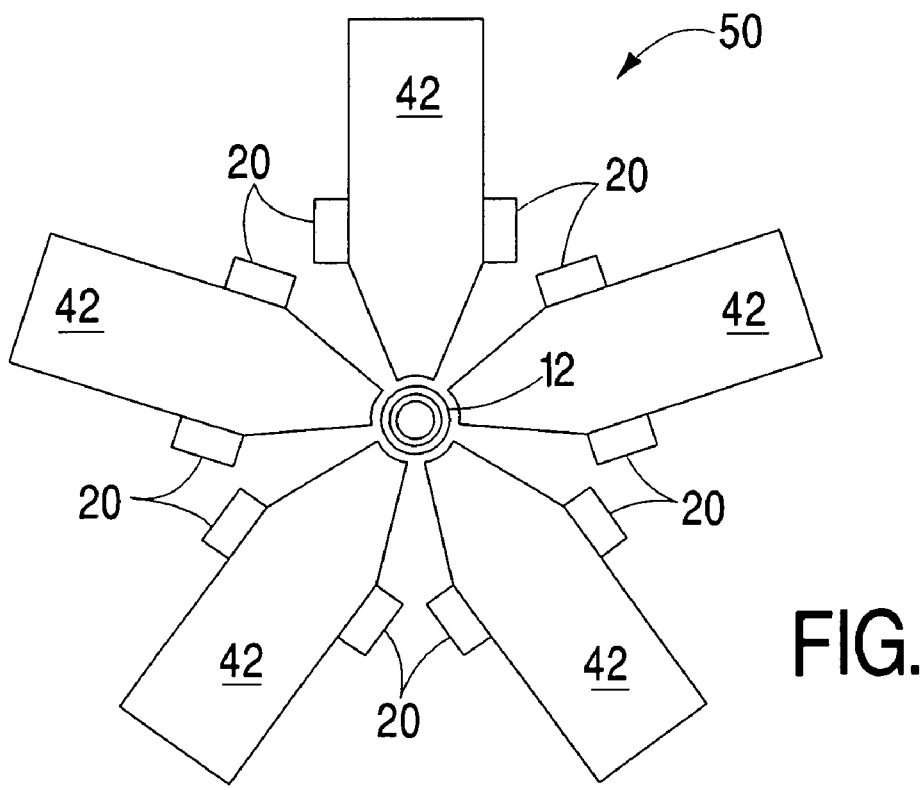
FIG. 3 schematically illustrates an embodiment of an apparatus for making a medical device.

Examples of stent crimping devices, as well as appropriate actuation devices and links, are described in Austin, U.S. Pat. No. 6,360,577, hereby incorporated by reference. Stent crimping devices are also commercially available, e.g., from Machine Solutions Inc. (Flagstaff, Ariz.). In other embodiments, referring to FIG. 2, a multi-jaw crimping device 40 is illustrated including a series of jaws 42 (as shown, three) arranged radially to engage and to crimp stent 12 (crimping direction B). Each jaw 42 can include one or more vibrators 20 (as shown, two on each jaw) to induce vibratory motion to the jaw, which is transmitted to stent 12. FIG. 3 shows a crimping device 50 having five jaws 42.

Figure 4:
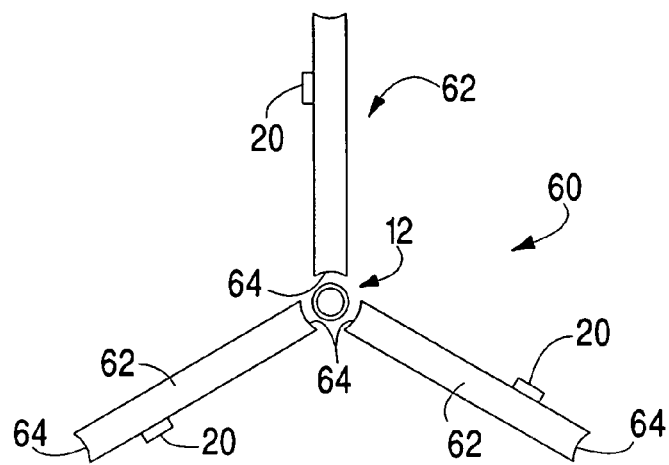
FIG. 4 schematically illustrates an embodiment of an apparatus for making a medical device.
Figure 5:
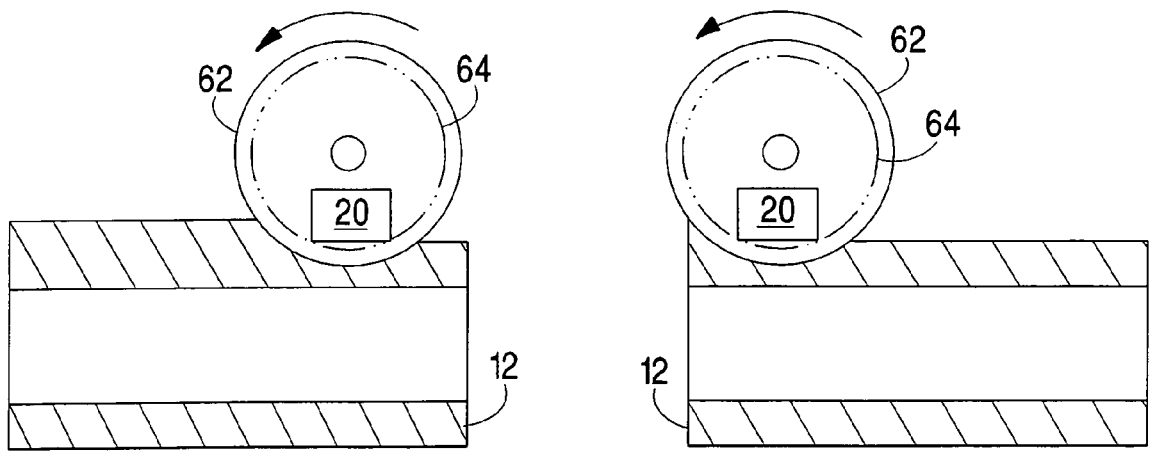
FIG. 5 schematically illustrates an embodiment of a method of making a medical device.

FIG. 4 shows a crimping device 60 having one or more rollers 62 (as shown, three), and one or more vibrators 20 attached to the roller(s). As shown, roller 62 is a circular disc that has a groove 64 extending circumferentially around the disc. The size, e.g., curvature, of groove 64 is a function of the degree of crimping desired. In some modes of operation, stent 12 is first placed on a catheter system. Stent 12 may or may not be pre-crimped. The catheter system is then secured by passing a lumen of the catheter system over a mounting block having a mandrel (not shown), e.g., a horizontal tube. Vibratory energy is applied to rollers 62 via vibrators 20 as described herein. Rollers 62 then contact stent 12 (thereby transmitting vibrations to the stent) and are rolled along the longitudinal axis of the stent (FIG. 5) with a desired pressure, thereby radially reducing the stent. Rollers 62 having smaller grooves 64 can be used to further crimp stent 12. In some cases, vibratory energy is applied to rollers 62 after the rollers initially contact stent 12.

Figure 6:
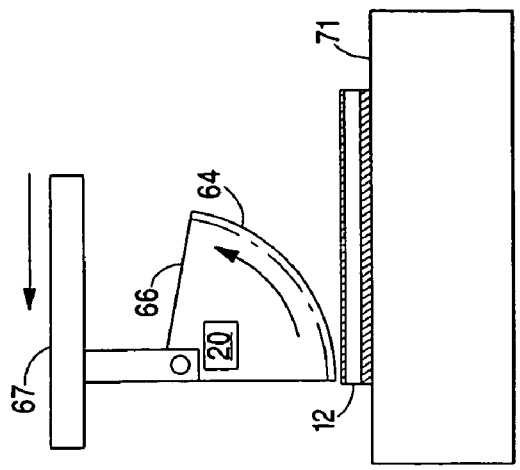
FIG. 6 schematically illustrates an embodiment of a method of making a medical device.
Figure 6:
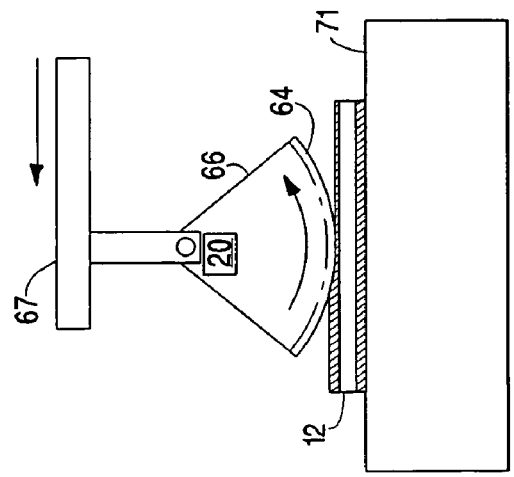
Figure 6:
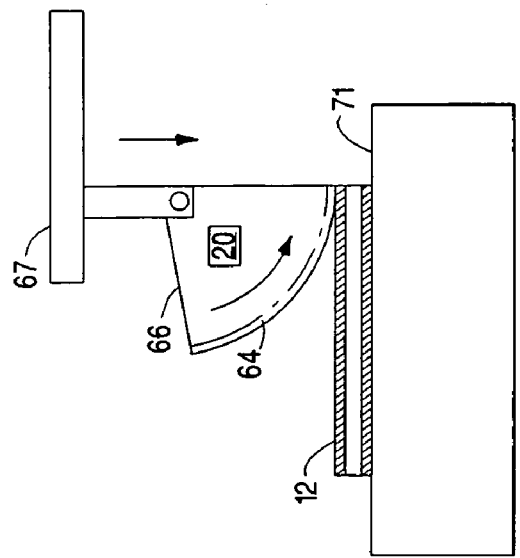

A non-circular roller can be used. For example, FIG. 6 shows a semi-circular, cam-like member 66 having a peripheral groove 64 configured to be rolled over stent 12, which can be pre-crimped to a support. Member 66 is linked to an arm 67. On some modes of operation, stent 12 is mounted on a catheter system and placed on a mounting block 71 (only the stent in FIG. 6). Next, arm 67 is moved for groove 64 to contact stent 12 at a desired force. Vibrational energy is then applied to member 66, and arm 67 is actuated (arrow C) to roll member 66 over stent 12, thereby radially reducing the stent.

Alternatively or in addition, stent 12 can be moved relative to roller(s) 62 or member 66 along the longitudinal axis of the stent. For example, referring to FIG. 4, rollers 62 can be held stationary while allowing the rollers to rotate about their respective center axes. With rollers 62 arranged to define an opening of a predetermined size, stent 12 is then moved along its longitudinal axis (as shown in FIG. 4, out of the plane of the paper) through the opening to effect crimping. Grooves 64 can be coated with a lubricious material, e.g., a polymer such as polytetrafluoroethylene (PTFE), for example, to reduce damage to stent 12.

Figure 7:
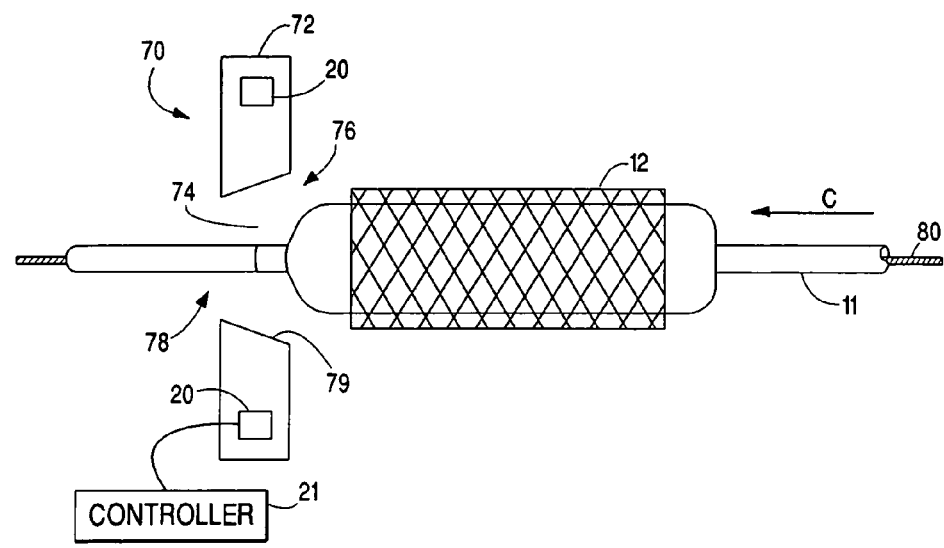
FIG. 7 schematically illustrates an embodiment of a method of making a medical device.
Figure 7:
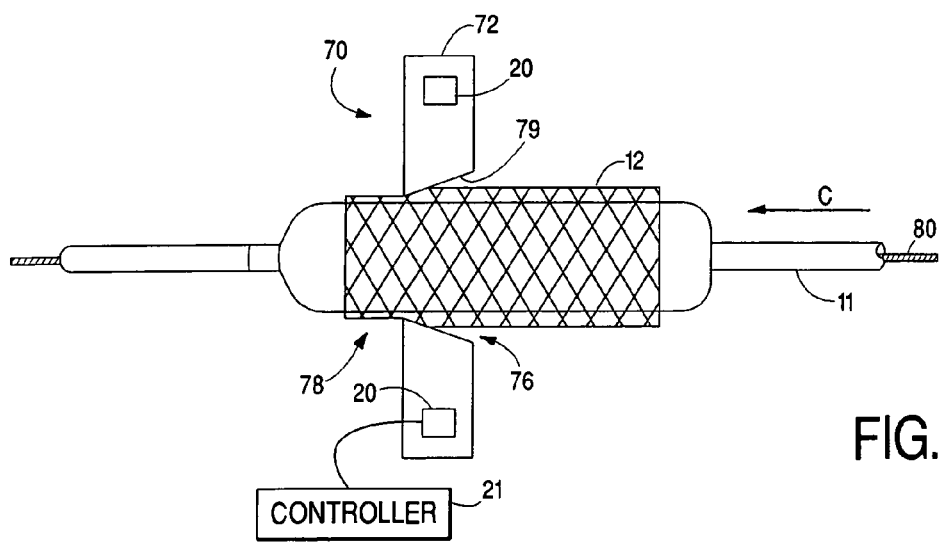
Figure 8:
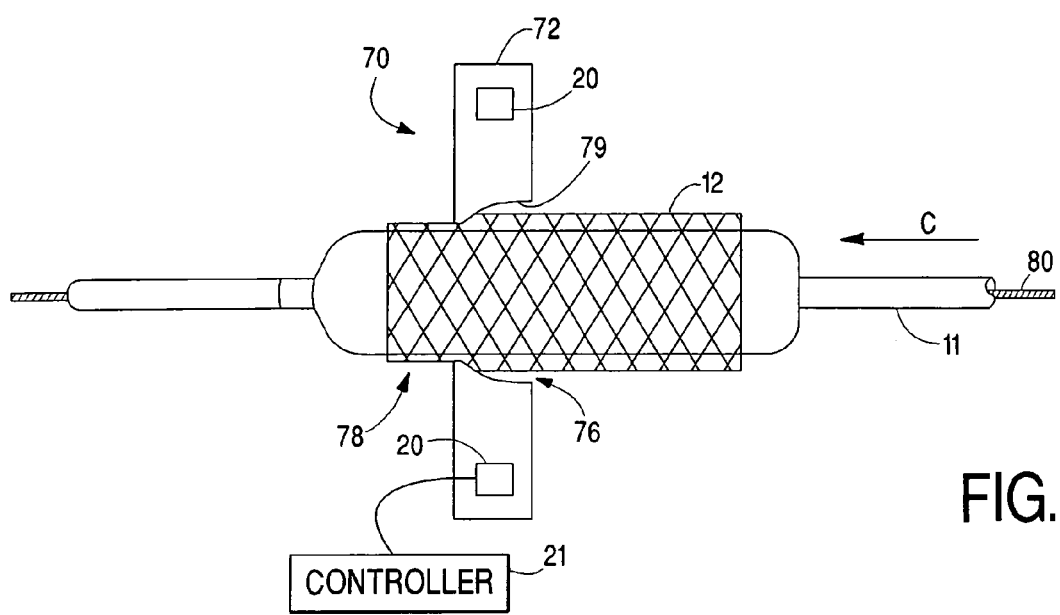
FIG. 8 schematically illustrates an embodiment of a method of making a medical device.

FIG. 7 shows another embodiment of a stent crimping device 70 including a forming die 72, e.g., a metal plate, and one or more vibrators 20 on the forming die. Die 72 includes a funnel-shaped opening 74 having an input side 76 and tapering to a relatively smaller output side 78. The degree of the tapering, relative to the center axis of opening 74, can range from about 10 to about 80 degrees. For example, the degree of tapering can be greater than or equal to about 10, 20, 30, 40, 50, 60, or 70 degrees; and/or less than or equal to about 80, 70, 60, 50, 40, 30, or 20 degrees. The diameter of output side 78 can be equal to or less than the final diameter of a stent crimped on a support. The inner wall 79 of opening 74 can be coated with a lubricious coating, e.g., a polymer such as PTFE, to enhance crimping or to reduce damage to stent 12. Alternatively or in addition, a polymer sleeve can be temporarily placed around stent 12 during crimping. In other embodiments, the inner wall 79 of opening 74 can be curved (FIG. 8).

In operation, vibrators 20 are actuated to vibrate forming die 72. Stent 12, which is placed on catheter system 11 supported by a mandrel 80, is then introduced into input side 76 of opening 74 (arrow C). As stent 12 contacts the wall of opening 74, the stent is radially reduced in size. As described above, the diameter of output side 78 can produce the final diameter of the crimped stent 12, but in some cases, the diameter of the output side 78 is less than the final diameter, e.g., to compensate for recoil of the stent. In some embodiments, forming die 72 is rotated about the center axis of opening 74 during operation. Multiple dies 72 can be placed in series to provide gradual crimping.

Turning now to vibrators 20, vibrators are configured to emit energy, e.g., harmonic vibrations and/or forced vibrations, to stent 12. Examples of vibrators 20 include mechanical transducers (e.g., spring mass/moving coil systems) or solid state transducers such as those having piezoelectric elements, available, e.g., from STAPLA Ultrasonics Corp. (Wilmington, Mass.) and Blatek Inc. (State College, Pa.). Vibrators 20 can be placed symmetrically or asymmetrically about device 18, depending, e.g., on the particularly crimping operation, the crimping device, and the medical device being made. Likewise, in embodiments, vibrator(s) 20 can be attached to one or more blades 24 and/or jaws 42. In some cases, the closer vibrator(s) 20 are to stent 12 and catheter system 11, the more energy is transferred to the stent and catheter system.

The vibratory energy that is applied during crimping can be a function of stent 12, catheter system 11, and/or apparatus 10, for example, their size, configuration, and material of construction. The frequency of the vibrations used during crimping can be determined empirically, according to a desired crimping result. In other embodiments, the frequency of the vibrations can be determined by measuring the vibration amplitude of apparatus 10 and/or stent 12 as a function of applied frequency, and applying the frequencies that provide selected amplitudes. Such techniques for determining operating frequencies are described, e.g., in U.S. Pat. Nos. 4,968, 359 and 3,741,820, hereby incorporated by reference. One or more frequencies can be used. The frequencies can change as a function of time and/or degree of crimping. In embodiments, frequencies can range from about 1000 kHz or less.

In operation, controller 21 activates crimping device 18 and ultrasonic vibrators 20 simultaneously. Activation of device 18 causes actuation plate 22 to rotate, e.g., clockwise, thereby causing blades 24 to move in such a manner as to narrow aperture 26 and compress stent 12. Meanwhile, vibrators 20 emit vibratory energy to plate 22, which transmits the energy to stent 12 and catheter system 11 via blades 24 and their links. In other embodiments, controller 21 activates crimping device 18 and vibrators 20 sequentially. For example, controller 21 can activate crimping device 18 to crimp stent 12 to a predetermined diameter (i.e., a stepped reduction), deactivate the device, activate vibrators 20 for a predetermined time, deactivate the vibrators, re-activate the crimping device to crimp the stent to smaller diameter, and so on.

Different methods of operation can provide different securement, e.g., different degrees of embedment, of stent 12. For example, vibratory energy may be applied to the endoprosthesis after it has been crimped. An endoprosthesis crimped without vibratory energy may be exposed to vibratory energy afterwards to relieve stress in the endoprosthesis and/or to enhance contact or nesting. Vibratory energy can also be applied to endoprostheses that are not crimped, such as self-expanding stents (e.g., Radius™, available from Boston Scientific Corp.-Scimed, Maple Grove, Minn.) or stents that are woven to a support with a string and implanted by withdrawing the string (e.g., Ultraflex™, Boston Scientific Corp.-Scimed). For coated endoprostheses, e.g., polymer-coated and/or drug-coated endoprostheses, vibratory energy may be applied, e.g., to reduce stress, to enhance dispersion of materials in the coating, and/or to increase contact between the coating and the endoprosthesis, Vibratory stress relief is discussed in "Vibratory Stress Relief-Massage For Your Workpieces" at wwww.mmsonline.com/articles/0501rt3.html; and "Formula 62 Resonant Vibration Method for Reducing Residual Stresses in Welded or Machined Fabrications" at www.exotech.nl.

After stent 12 is attached to catheter system 11, the stent and system can be used according to conventional methods. Suitable stent delivery techniques are exemplified by the NIR on Ranger® system, available from Boston Scientific Scimed, Maple Grove, Minn.

Generally, stent 12 can be a conventional stent, e.g., balloon expandable, self-expandable, or a combination of both. Stent 12 can also be a part of a stent-graft. The stent-graft can be a stent attached to a biocompatible, non-porous or semi-porous polymer matrix made of polytetrafluoroethylene (PTFE), expanded PTFE, polyethylene, DACRON™, urethane, or polypropylene. Stent 12 can include a releasable therapeutic agent or a pharmaceutically active compound, such as described in U.S. Pat. No. 5,674,242, and commonly-assigned U.S. Ser. No. 09/895,415, filed Jul. 2, 2001. The therapeutic agents or pharmaceutically active compounds can include, for example, anti-thrombogenic agents, antioxidants, anti-inflammatory agents, anesthetic agents, anti-coagulants, and antibiotics. The stent is typically formed of a metal body such as a mesh. Examples of stent 12 are described in U.S. Pat. Nos. 5,725,570, 5,366,504, and 5,234,457. Suitable catheter systems are described in, for example, Wang U.S. Pat. No. 5,195,969, and Hamlin U.S. Pat. No. 5,270,086.

OTHER EMBODIMENTS

Figure 9:
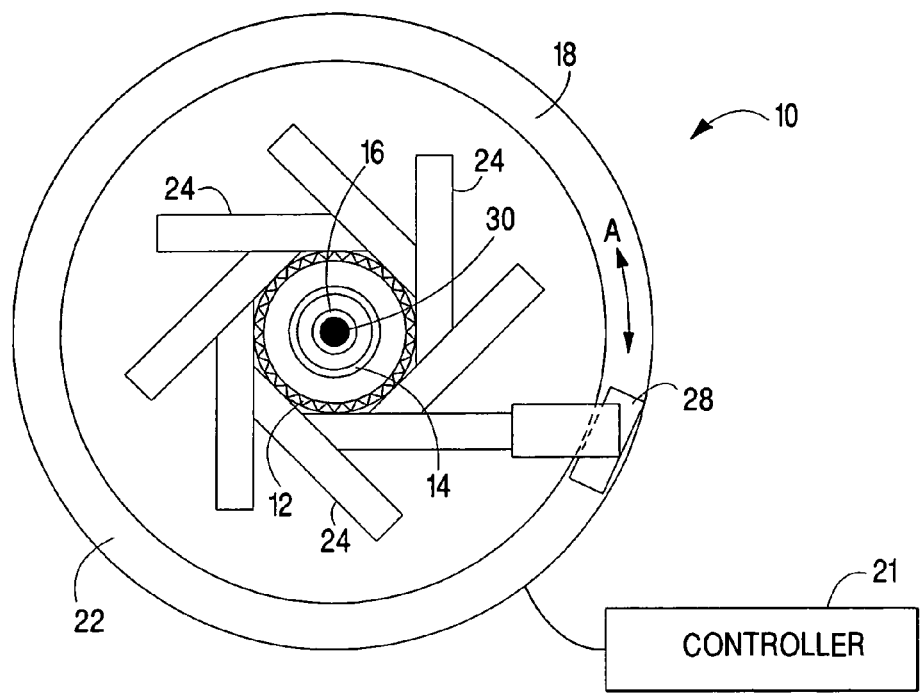
FIG. 9 schematically illustrates an embodiment of a method of making a medical device.

In other embodiments, vibratory energy can be applied from within the catheter system 11. Referring to FIG. 9, a mandrel 30, such as a tube or a hypotube, can be inserted into catheter 16. Vibratory energy can then be applied from within catheter system 11, for example, by connecting mandrel 30 to a transducer that is capable of transmitting energy along the mandrel. Mandrel 30 can be used with or without vibrators 20 external to catheter system 11.

Vibratory energy can also be applied without vibrators 20 being in direct contact with stent crimping device 18. For example, the crimping process can be performed in a medium that is capable of transmitting vibratory energy, such as by submerging apparatus 10 in sterile water in a vibratory bath, e.g., an ultrasonic bath. The vibratory bath can also clean the catheter system and stent, and cavitation bubbles imploding can create shock waves that enhance vibrations. Ultrasonic baths are available, e.g., from Electron Microscopy Sciences (Fort Washington, Pa.) or Dr. Hielscher GmbH (Teltow, Germany). Vibratory energy can also be transmitted through air, e.g., by using a speaker capable of emitting vibratory frequencies, e.g., ultrasonic frequencies. Other mediums through which vibratory energy can be transmitted include, e.g., a plasma medium, or a supersaturated vapor medium.

In some embodiments, heat is applied to any of the crimping devices described herein, stent 12, and/or catheter system 11 during crimping. The heat can soften balloon 14, thereby allowing stent 12 to nest well in the balloon. The heat can also relieve stress in stent 12, e.g., as in annealing. The heat can be applied, for example, by an infrared light source, by performing the crimping process in a heated environment (e.g., an oven), by placing a heatable mandrel in catheter 16, by heating the ultrasonic water bath, and/or by heating the crimping devices, e.g., resistively. Heat can also be generated due to friction between blades 24, stent 12, and balloon 14. The heating temperature will depend, e.g., on the stent material and/or the balloon material. More than one heating temperatures can be used. In embodiments, heating temperatures range from about 25° C. to about 100° C.

In other embodiments, the crimping device, stent 20, and/or catheter system 11 can be cooled during crimping. The temperature can be reduced by conduction or by convection. For example, a cold gas flow can be directed to the crimping device, stent 20, and/or catheter system 11; or the crimping device, the stent, and/or the catheter system can be immersed in a cold bath, e.g., a liquid nitrogen bath (to about −200° C.).

Figure 10:
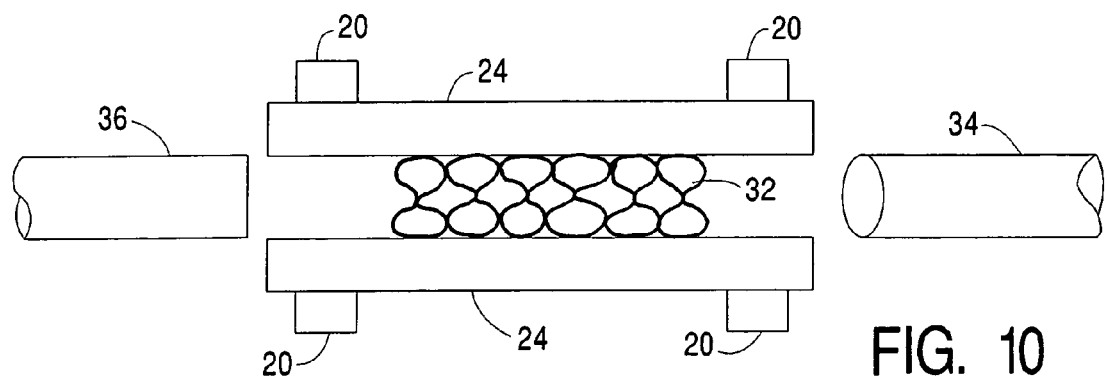
FIG. 10 schematically illustrates an embodiment of a method of making a medical device.

The method of crimping stent 12 described above can also be applied to endoprostheses that are self-expandable or a combination of self-expandable and balloon-expandable. For example, referring to FIG. 10, a self-expandable stent 32 can be compressed as described above, and inserted into a sheath 34 using a plunger 36. Blades 24 can be coated with a lubricious layer, e.g., one including Teflon® (polytetrafluoroethylene), to allow plunger 36 to easily move stent 32 and to reduce damage to the stent. In embodiments, sheath 34 and/or plunger 36 may include vibrator(s) 20, e.g., by using a mandrel that can be vibrated such as mandrel 30.

Two or more apparatuses 10 can be placed sequentially to provide differential compression along a stent. For example, a stent may include end portions that are self-expandable and a middle portion that is balloon-expandable (e.g., as in U.S. Pat. No. 5,674,276), or a stent may include different materials along its length. Different compression forces may be required along the length of the stents to provide a desired compression profile, so using a plurality of adjacent crimping devices allows selected portions of the stent to receive selected compression forces. Such arrangements of crimping devices are described, e.g., in U.S. Pat. No. 6,360,577.

In general, the crimping apparatuses can have any combination of vibrators or be used with any vibrating methods described herein.

Vibratory energy can be used to enhance performance of medical devices other than endoprostheses. For example, other expandable medical devices such as arterial or venous filters can be treated with vibratory energy to reduce stress. Medical balloons can be treated with vibratory energy. For example, angioplasty balloons are typically wrapped about a catheter in a multi-lobe or winged configuration. Vibratory energy can be provided to the wrapped balloon to settle the balloon lobes to a small diameter or vibratory energy can be applied during wrapping by applying the energy to a wing-forming tool. A suitable wing-forming tool is described in U.S. Pat. No. 5,456,666, and references therein, and a filter is described in Simon, U.S. Pat. No. 4,425,908.

The methods described above can also be used to attach band(s) (e.g., marker bands that are radiopaque or magnetopaque, i.e., visible by magnetic resonance imaging (MRI)) to various supports. Examples of supports include catheters, balloons, guidewires, sheath introducers, temporary filters (e.g., non-metallic, such as ceramic or polymeric, filters), stents, and grafts. In some embodiments, the band(s) can be placed on the support, e.g., slipped-fit around a polymer shaft, and the band(s) can be compressed as described herein. Suitable materials for the bands include, for example, gold, platinum, tungsten, tantalum, and metal alloys containing a sufficient percentage of heavy elements. Suitable magnetopaque materials include, for example, non-ferrous metal-alloys containing paramagnetic elements (e.g., dysprosium or gadolinium) such as terbium-dysprosium, dysprosium, and gadolinium; non-ferrous metallic bands coated with an oxide or a carbide layer of dysprosium or gadolinium (e.g., $Dy_2O_3$ or $Gd_2O_3$); non-ferrous metals (e.g., copper, silver, platinum, or gold) coated with a layer of superparamagnetic material, such as nanocrystalline $Fe_3O_4$, $CoFe_2O_4$, $MnFe_2O_4$, or $MgFe_2O_4$; and nanocrystalline particles of the transition metal oxides (e.g., oxides of Fe, Co, Ni).

All publications, applications, and patents referred to herein are incorporated by reference in their entirety.

Other embodiments are within the claims.

What is claimed is:

1. A method of manufacturing an endoprosthesis, the method comprising:
   providing an endoprosthesis having an outer diameter;
   reducing the outer diameter of the endoprosthesis, the reduction in outer diameter of the endoprosthesis secures the endoprosthesis to a catheter; and
   vibrating the endoprosthesis,
   wherein the endoprosthesis is vibrated simultaneously with the reduction in outer diameter of the endoprosthesis.

2. The method of claim 1, wherein the endoprosthesis is vibrated ultrasonically.

3. The method of claim 1, wherein the reduction in outer diameter of the endoprosthesis secures the endoprosthesis to a balloon.

4. The method of claim 1, wherein the entire endoprosthesis is reduced in outer diameter.

5. The method of claim 1, wherein only a portion of the endoprosthesis is reduced in outer diameter.

6. The method of claim 1, wherein the endoprosthesis is vibrated from within the endoprosthesis.

7. The method of claim 1, wherein the endoprosthesis is vibrated externally of the endoprosthesis.

8. The method of claim 1, further comprising heating the endoprosthesis.

9. The method of claim 1, further comprising cooling the endoprosthesis.

10. The method of claim 1, wherein vibratory energy is directed to the endoprosthesis through a gaseous medium.

11. The method of claim 1, wherein vibratory energy is directed to the endoprosthesis through a liquid medium.

12. The method of claim 1, wherein vibratory energy is directed to the endoprosthesis through a plasma.

13. The method of claim 1, wherein vibratory energy is directed to the endoprosthesis through a supersaturated vapor medium.

14. The method of claim 1, wherein the endoprosthesis is vibrated at harmonic or subharmonic frequencies.

15. The method of claim 1, wherein the endoprosthesis is vibrated at less than about 1,000 kiloHertz.

16. The method of claim 1, wherein the endoprosthesis is vibrated at multiple frequencies.

17. The method of claim 1, wherein the endoprosthesis is vibrated at one or more frequencies that vary as a function of time.

18. The method of claim 1, wherein the endoprosthesis comprises a stent.

19. The method of claim 18, wherein the stent comprises a drug-releasing layer.

20. The method of claim 1, wherein the endoprosthesis comprises a stent-graft.

21. The method of claim 1, wherein reducing the outer diameter of endoprosthesis comprises contacting the endoprosthesis in a longitudinal direction with a member.

22. The method of claim 1, wherein reducing the outer diameter of endoprosthesis comprises contacting the endoprosthesis in a longitudinal direction with a roller having a groove.

23. A method of manufacturing an endoprosthesis, the method comprising:
   radially reducing the size of the endoprosthesis, the reduction in size of the endoprosthesis securing the endoprosthesis to a support; and
   simultaneously applying vibratory energy to the endoprosthesis;
   wherein radially reducing the size of the endoprosthesis secures the endoprosthesis to a balloon.

24. The method of claim 23, wherein the vibratory energy is ultrasonic energy.

25. The method of claim 23, further comprising heating the endoprosthesis.

26. The method of claim 23, further comprising cooling the endoprosthesis.

27. The method of claim 23, wherein the endoprosthesis comprises a stent.

28. The method of claim 23, wherein the endoprosthesis comprises a drug-releasing layer.

29. A method, comprising:
   providing an endoprosthesis including a metal body and a polymer layer;
   crimping the endoprosthesis; and
   applying vibratory energy to the endoprosthesis, wherein vibratory energy is applied during crimping.

30. The method of claim 29, wherein the polymer layer is on an outside surface of the metal body.

31. The method of claim 29, wherein the polymer layer includes a drug.

32. The method of claim 29, wherein the polymer layer is a continuous polymer tubular member.

33. The method of claim 29, wherein the polymer include polytetrafluoroethylene.

34. The method of claim 29, wherein the endoprosthesis is balloon-expandable.

35. The method of claim 29, wherein vibratory energy is applied by contacting a vibrating member to the endoprosthesis.

36. The method of claim 29, wherein the vibratory energy has a frequency of less than about 1,000 kiloHertz.

37. A method of manufacturing an expandable medical device, the method comprising:
   placing the expandable medical device into a crimping apparatus;
   reducing the size of the expandable medical device;
   applying vibratory energy to the expandable medical device; and
   removing the expandable medical device from the crimping apparatus.

38. The method of claim 37, wherein the expandable medical device is an endoprosthesis.

39. The method of claim 37, wherein vibratory energy is applied to the expandable medical device simultaneously with the reduction in size of the expandable medical device.

40. The method of claim 37, wherein vibratory energy is applied to the expandable medical device subsequent to the reduction in size of the expandable medical device.

41. The method of claim 37, wherein the expandable medical device is radially reduced in size.

42. The method of claim 37, wherein the expandable medical device is a stent.

43. The method of claim 37, wherein the crimping apparatus comprises a first device capable of applying a radial inward force to the expandable medical device and a second device capable of applying energy to the expandable medical device.

44. The method of claim 43, wherein the first device is a stent crimping device.

45. The method of claim 43, wherein the second device is a vibrator.

46. The method of claim 43, wherein the second device contacts the first device.

47. A method of manufacturing an expandable medical device, the method comprising, in sequence:

(a) placing the expandable medical device into a crimping apparatus;
(b) reducing the size of the expandable medical device by applying radial inward energy to the expandable medical device;
(c) applying a vibratory energy to the expandable medical device; and
(d) removing the expandable medical device from the crimping apparatus.

* * * * *